United States Patent
Chungi et al.

(12) 
(10) Patent No.: US 6,669,955 B2
(45) Date of Patent: *Dec. 30, 2003

US006669955B2

(54) COMBINATION DOSAGE FORM CONTAINING INDIVIDUAL DOSAGE UNITS OF A CHOLESTEROL-LOWERING AGENT, AN INHIBITOR OF THE RENIN-ANGIOTENSIN SYSTEM, AND ASPIRIN

(75) Inventors: Shubha Chungi, Sharon, MA (US); Theodore L. Iorio, Millis, MA (US)

(73) Assignee: Longwood Pharmaceutical Research, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/941,948

(22) Filed: Aug. 28, 2001

(65) Prior Publication Data

US 2003/0068366 A1 Apr. 10, 2003

(51) Int. Cl.$^7$ .............................. A61K 9/20; A61K 9/22; A61K 9/24; A61K 9/48
(52) U.S. Cl. ..................... 424/464; 424/451; 424/452; 424/465; 424/468; 424/472
(58) Field of Search ................. 424/451, 452, 424/464, 465, 468, 472; 514/85, 91

(56) References Cited

U.S. PATENT DOCUMENTS

| | | | |
|---|---|---|---|
| 5,140,012 A | | 8/1992 | McGovern et al. |
| 5,157,025 A | | 10/1992 | Aberg et al. |
| H1286 H | * | 2/1994 | Eisman et al. ................. 514/91 |
| 5,298,497 A | * | 3/1994 | Tschollar et al. ............. 514/91 |
| 5,461,039 A | | 10/1995 | Tschollar et al. |
| 5,593,971 A | | 1/1997 | Tschollar et al. |
| 5,622,985 A | * | 4/1997 | Olukotun et al. ........... 514/423 |
| 6,235,311 B1 | * | 5/2001 | Ullah et al. .................. 424/472 |
| 6,248,729 B1 | * | 6/2001 | Coniglio et al. .............. 514/85 |
| 6,251,852 B1 | * | 6/2001 | Gould et al. .................... 514/2 |

FOREIGN PATENT DOCUMENTS

| | | | |
|---|---|---|---|
| EP | 0457514 | | 8/1996 |
| EP | 0622078 | | 9/1999 |
| WO | WO 01/15674 | | 3/2001 |
| WO | 01/15674 | * | 3/2001 |

OTHER PUBLICATIONS

Fonarow et al. "Rationale and Design of the Cardiac Hospitalization Atheroscherosis Management Program at the University o California Los Angeles", pp. 10A–17A, Am. J. Cardiol. 85.*

Fonarow et al. (2000), "Rationale and Design of the Cardiac Hospitalization Atherosclerosis Management Program at the University of California Los Angeles," *Am. J. Cardiol.* 85:10A–17A.

Fonarow et al. (2001), "Improved Treatment of Coronary Heart Disease by Implementation of a Cardiac Hospitalization Atherosclerosis Management Program (CHAMP)," *Am. J. Cardiol.* 87:819–822.

* cited by examiner

*Primary Examiner*—Thurman K. Page
*Assistant Examiner*—S. Tran
(74) *Attorney, Agent, or Firm*—Reed & Eberle LLP; Dianne E. Reed; Karen Canaan

(57) ABSTRACT

An orally administrable pharmaceutical formulation is provided that combines, as active agents, a cholesterol-lowering agent, an inhibitor of the renin-angiotensin system, aspirin, and optionally at least one of vitamin $B_6$, $B_{12}$, and folate; the active agents are each present in a unit dose appropriate for once-daily dosing, and at least one of the active agents is contained in a dosage unit within the dosage form that physically separates it from the other active agents. The formulation is provided as a simple and convenient therapy to reduce the risk of cardiovascular events in individuals who are at elevated cardiovascular risk, including individuals who have systemic lupus erythematosus. The formulation is also therapeutic for individuals during or immediately following an occurrence of acute myocardial infarction.

59 Claims, No Drawings

US 6,669,955 B2

COMBINATION DOSAGE FORM CONTAINING INDIVIDUAL DOSAGE UNITS OF A CHOLESTEROL-LOWERING AGENT, AN INHIBITOR OF THE RENIN-ANGIOTENSIN SYSTEM, AND ASPIRIN

TECHNICAL FIELD

This invention relates generally to pharmaceutical formulations for treating patients at elevated cardiovascular risk, and more particularly relates to dosage forms that combine a cholesterol-lowering agent, an inhibitor of the renin-angiotensin system, and aspirin.

BACKGROUND

Many individuals are at an elevated risk of suffering serious to life-threatening cardiovascular events, such as myocardial infarction (heart attack), cardiac arrest, congestive heart failure, stroke, peripheral vascular disease, and/or claudication. The risk factors are numerous and widespread throughout the world population. They include cigarette smoking, diabetes, hypercholesterolemia (high serum cholesterol), hypertension, angina, systemic lupus erythematosus, prior heart attacks or strokes, hemodialysis, hyperhomocysteine levels, obesity, sedentary lifestyle, receiving an organ transplant, and others. Many of these risk factors are mediated through atherosclerosis, which is a major risk factor for cardiovascular events. There is a need for a safe and convenient pharmaceutical formulation that would effectively reduce the risk of incurring a cardiovascular event in individuals who have these risk factors.

Olukotun et al., in U.S. Pat. No. 5,622,985, disclose that inhibitors of 3-hydroxy-3-methylglutaryl coenzyme A (HMG CoA) reductase (cholesterol-lowering drugs), particularly pravastatin, when used alone or with an angiotensin converting enzyme (ACE) inhibitor, decrease the risk of a second heart attack in a patient who has a substantially normal cholesterol level. The combination with an ACE inhibitor is optional, and no mention is made of combining HMG CoA reductase inhibitors with other inhibitors of the renin-angiotensin system or with aspirin. In addition, the prevention of cardiovascular events other than second heart attacks is not considered.

Similarly, McGovern et al., in U.S. Pat. No. 5,140,012, disclose the use of pravastatin alone, or in combination with an ACE inhibitor, to prevent the onset of restenosis following angioplasty. HMG CoA reductase inhibitors other than pravastatin are not considered, and no mention is made of combining HMG CoA reductase inhibitors with other inhibitors of the renin-angiotensin system or with aspirin. The prevention of cardiovascular disorders other than restenosis following angioplasty is not considered.

U.S. Pat. Nos. 5,461,039 and 5,593,971 to Tschollar et al. disclose the use of a cholesterol-lowering drug, alone or in combination with an ACE inhibitor, to inhibit hypertension in a normotensive individual who has insulin resistance. No mention is made of combining cholesterol-lowering drugs with inhibitors of the renin-angiotensin system other than ACE inhibitors or with aspirin. In addition, the disclosed methods are limited to normotensive individuals who are insulin resistant, and no mention is made of directly preventing cardiovascular events.

Eisman et al., in U.S. Statutory Invention Registration No. H1286, disclose a method for treating peripheral atherosclerotic disease and/or intermittent claudication by use of one or more cholesterol-lowering drugs by themselves or together with an ACE inhibitor, or by use of an ACE inhibitor alone. No mention is made of combining cholesterol-lowering drugs with inhibitors of the renin-angiotensin system other than ACE inhibitors or with aspirin. The treatment or prevention of cardiovascular disorders other than peripheral atherosclerotic disease and/or intermittent claudication is not considered.

Bergey et al., in European Patent Specification EP 457,514, disclose the use of a cholesterol-lowering drug together with an ACE inhibitor to prevent, stabilize, or cause regression of atherosclerosis. No mention is made of combining cholesterol-lowering drugs with inhibitors of the renin-angiotensin system other than ACE inhibitors or with aspirin. The treatment or prevention of cardiovascular disorders other than atherosclerosis is not considered.

U.S. Pat. No. 6,235,311 to Ullah et al. discloses pharmaceutical compositions that contain a statin (HMG CoA reductase inhibitor) plus aspirin, optionally containing vitamins $B_6$, $B_{12}$, or folic acid, and methods of their use for: lowering serum cholesterol; preventing, inhibiting, or treating atherosclerosis; or reducing the risk of or treating a cardiovascular event or disease, coronary artery disease, or cerebrovascular disease. This reference makes no mention of, or considers in any way, inhibitors of the renin-angiotensin system.

Coniglio et al., in U.S. Pat. No. 6,248,729, disclose a method for preventing a cerebral infarction by administering to a patient a combination of an ADP-receptor blocking antiplatelet drug, an antihypertensive agent (such as an angiotensin II antagonist, an ACE inhibitor, or an ACE/NEP inhibitor), and optionally, a cholesterol-lowering drug and/or aspirin. Pharmaceutical compositions comprising combinations of these agents are also disclosed. The disclosed methods and compositions, however, require an ADP-receptor blocking antiplatelet drug (which does not include aspirin) and do not mention or consider cardiovascular events other than a cerebral infarction.

Schoelkens et al., in International Patent Publication No. WO 01/15674, disclose the use of an inhibitor of the renin-angiotensin system, optionally together with another antihypertensive drug, a cholesterol-lowering drug, a diuretic, or aspirin, in the prevention of cardiovascular events. Also disclosed is a combination product for this purpose containing an inhibitor of the renin-angiotensin system and a cholesterol-lowering agent. Further disclosed is the use of an inhibitor of the renin-angiotensin system together with another antihypertensive, or a cholesterol-lowering agent, or a diuretic, or aspirin in the manufacture of a medicament for the prevention of cardiovascular events. Never mentioned or considered is the possibility of combining three or more active agents, either in a method for the treatment of a patient or in the manufacture of a pharmaceutical product. Even though certain inhibitors of the renin-angiotensin system, cholesterol-lowering agents, and aspirin are mentioned, and combination therapies involving inhibitors of the renin-angiotensin system together with a cholesterol-lowering agent or aspirin are disclosed, no consideration is made of combining all three in a single dosage form.

SUMMARY OF THE INVENTION

Accordingly, it is a primary object of the invention to provide a pharmaceutical composition that overcomes the limitations of the above-described formulations and dosage forms.

It is an object of the invention to provide a once-daily orally administrable pharmaceutical composition for treating a patient at elevated cardiovascular risk, the composition comprising a single dosage form containing a combination of therapeutically effective unit dosages of a cholesterol-lowering agent, an inhibitor of the renin-angiotensin system, aspirin, and optionally one or more of vitamin $B_6$, vitamin $B_{12}$, and folic acid, plus a pharmaceutically acceptable carrier, wherein each unit dosage is a daily dose and at least one of the active agents is present in a dosage unit within the dosage form that physically separates it from the other active agents.

It is another object of the invention to provide an orally administrable solid dosage form wherein at least two of the active agents are present in dosage units that physically separate them from the other active agents and from each other.

Another object of the invention is to provide an orally administrable solid dosage form wherein at least one of the active agents is present in a controlled release dosage unit, i.e., a sustained release and/or delayed release dosage unit.

Another object of the invention is to provide such compositions wherein the cholesterol-lowering agent is an HMG CoA reductase inhibitor, and the inhibitor of the renin-angiotensin system is an ACE inhibitor or an angiotensin II antagonist.

It is still another object of the invention to provide such compositions wherein all three of vitamin $B_6$, vitamin $B_{12}$, and folic acid are incorporated therein.

Additional objects, advantages and novel features of the invention will be set forth in part in the description which follows, and in part will become apparent to those skilled in the art upon examination of the following, or may be learned by practice of the invention.

The present invention provides a once-daily oral dosage form comprising a combination of a therapeutically effective unit dose of a cholesterol-lowering agent, a therapeutically effective unit dose of an inhibitor or the renin-angiotensin system, and a therapeutically effective unit dose of aspirin, optionally further combined with at least one vitamin B substance, wherein at least one of the active agents is present in a dosage unit within the dosage form that physically separates it from the other active agents. Preferably, at least two of the active agents are present in dosage units that physically separate them from the other active agents and from each other, and still more preferably, at least one of the active agents is present in a controlled release dosage unit, i.e., a sustained release and/or delayed release dosage unit. The invention also provides a method for treating a patient at elevated cardiovascular risk by administering the dosage form on a daily basis. As described in co-pending U.S. patent application Ser. No. 09/942,084 to Liang et al., filed on even date herewith, the aforementioned dosage form provides a safe and effective method for reducing the risk of cardiovascular events in these patients, by providing a single oral dosage form containing the aforementioned combination of active agents, which is conveniently administered once per day, wherein any detrimental interaction between active agents is minimized or eliminated. Such a simple regime has a high degree of patient compliance, leading to substantially improved efficacy. The combination of three or more active ingredients provides the additional advantage of possibly allowing reduced dosages of the active ingredients, increasing the safety of the therapy.

In a preferred embodiment, the dosage form of the invention comprises:

approximately 10 mg to approximately 120 mg, preferably approximately 25 mg to approximately 90 mg, of an HMG CoA reductase inhibitor selected from the group consisting of atorvastatin, fluvastatin, lovastatin, pravastatin, and simvastatin;

approximately 1 mg to approximately 60 mg, preferably approximately 15 mg to approximately 45 mg, of an ACE inhibitor selected from the group consisting of captopril, enalapril, fosinopril, lisinopril, quinapril, ramipril, and trandolapril;

approximately 20 mg to approximately 600 mg, preferably approximately 20 mg to approximately 150 mg, of aspirin; and, optionally, at least one of approximately 25 mg to approximately 75 mg, preferably approximately 40 mg to approximately 60 mg, of vitamin $B_6$;

approximately 0.25 mg to approximately 2 mg, preferably approximately 0.5 mg to approximately 1.5 mg, of vitamin $B_{12}$; and approximately 0.5 mg to approximately 8 mg, preferably approximately 1.5 mg to approximately 5 mg, of folic acid.

DETAILED DESCRIPTION OF THE INVENTION

I. Definitions and Nomenclature

Before describing the present invention in detail, it is to be understood that this invention is not limited to specific dosage forms, carriers, or the like, as such may vary. It is also to be understood that the terminology used herein is for the purpose of describing particular embodiments only, and is not intended to be limiting.

It must be noted that as used in this specification and the appended claims, the singular forms "a," "an", and "the" include plural referents unless the context clearly dictates otherwise. Thus, for example, reference to "an active agent" or "a pharmacologically active agent" includes a single active agent as well as two or more different active agents in combination, reference to "a carrier" includes mixtures of two or more carriers as well as a single carrier, and the like.

In describing and claiming the present invention, the following terminology will be used in accordance with the definitions set out below.

The terms "active agent," "pharmacologically active agent" and "drug" are used interchangeably herein to refer to a chemical compound that induces a desired pharmacological, physiological effect. The primary active agents herein are cholesterol-lowering agents, inhibitors of the renin-angiotensin system, and aspirin; other active agents include vitamin $B_6$, vitamin $B_{12}$, and folate. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, or when an active agent such as an HMG CoA reductase inhibitor or an ACE inhibitor is specifically identified, it is to be understood that applicants intend to include the active agent per se as well as pharmaceutically acceptable, pharmacologically active salts, esters, amides, prodrugs, metabolites, analogs, etc.

The terms "cholesterol-lowering agent" and "cholesterol-lowering drug" as used herein refer to a pharmacologically active, pharmaceutically acceptable agent that, when administered to a human subject who has hypercholesterolemia, has the effect of beneficially modifying serum cholesterol levels. More particularly, the cholesterol-lowering agent lowers serum low density lipoprotein (LDL) cholesterol levels, or inhibits oxidation of LDL cholesterol, whereas high density lipoprotein (HDL) serum cholesterol levels may be lowered, remain the same, or be increased. Preferably, the cholesterol-lowering agent brings the serum levels of LDL cholesterol and HDL cholesterol (and, more preferably, triglyceride levels) to normal or nearly normal levels.

The term "inhibitor of the renin-angiotensin system" as used herein refers to a pharmacologically active, pharmaceutically acceptable agent that inhibits, directly or indirectly, the adverse effects of angiotensin, particularly angiotensin II. Included, without limitation, are agents that: inhibit angiotensin II synthesis; inhibit angiotensin II binding to the $AT_1$, receptor; or inhibit renin activity.

By "pharmaceutically acceptable," such as in the recitation of a "pharmaceutically acceptable carrier," or a "pharmaceutically acceptable acid addition salt," is meant herein a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active"), as in a "pharmacologically active" derivative or metabolite, refers to a derivative or metabolite having the same type of pharmacological activity as the parent compound and approximately equivalent in degree. When the term "pharmaceutically acceptable" is used to refer to a derivative (e.g., a salt) of an active agent, it is to be understood that the compound is pharmacologically active as well, i.e., therapeutically effective to reduce elevated cardiovascular risk.

"Carriers" or "vehicles" as used herein refer to conventional pharmaceutically acceptable carrier materials suitable for drug administration, and include any such materials known in the art that are nontoxic and do not interact with other components of a pharmaceutical composition or drug delivery system in a deleterious manner.

The term "controlled release" is intended to refer to any drug-containing formulation in which release of the drug is not immediate, i.e., with a "controlled release" formulation, oral administration does not result in immediate release of the drug into an absorption pool. The term is used interchangeably with "nonimmediate release" as defined in *Remington: The Science and Practice of Pharmacy, Nineteenth Ed.* (Easton, Pa.: Mack Publishing Company, 1995). As discussed therein, immediate and nonimmediate release can be defined kinetically by reference to the following equation:

$$\text{Dosage Form} \xrightarrow{k_r \text{ drug release}} \text{Absorption Pool} \xrightarrow{k_a \text{ absorption}} \text{Target Area} \xrightarrow{k_e \text{ elimination}}$$

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release, $k_r$, is far greater than the absorption rate constant $k_a$. For the controlled release formulations, i.e., for the formulations of the present invention, the opposite is true, i.e., $k_r \ll k_a$, such that the rate of release of drug from the dosage form is the rate-limiting step in the delivery of the drug to the target area. The term "controlled release" as used herein is intended to include any nonimmediate release formulation, including but not limited to sustained release, delayed release and pulsatile release formulations.

The term "sustained release" is used in its conventional sense to refer to a drug formulation that provides for gradual release of drug over an extended period of time, and that preferably, although not necessarily, results in substantially constant blood levels of drug over an extended time period.

The term "delayed release" is used in its conventional sense to refer to a drug formulation in which there is a time delay provided between oral administration of a drug dosage form and the release of the drug therefrom. "Delayed release" may or may not involve gradual release of drug over an extended period of time, and thus may or may not be "sustained release." The preferred "controlled release" formulations herein are "delayed release," and particularly preferred "delayed release" formulations are enterically coated compositions.

"Enteric coating" or "enterically coated" as used herein relates to the presence of polymeric materials in a drug formulation that result in an increase in the drug's resistance to disintegration in the stomach. Typically, the polymeric material is present as a coating surrounding a drug-containing core, but the polymeric material may also be present in admixture with the drug itself within a coated formulation.

By an "effective" amount or a "therapeutically effective amount" of a drug or pharmacologically active agent is meant a nontoxic but sufficient amount of the drug or agent to provide the desired effect. In the combination therapy of the present invention, an "effective amount" of one component of the combination is the amount of that compound that is effective to provide the desired effect when used in combination with the other components of the combination. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual.

The term "elevated cardiovascular risk" as used herein refers to an increased risk of incurring a cardiovascular event, peripheral vascular disease, coronary heart disease, restenosis, or atherosclerosis in an individual, such risk being due to disorders, diseases, genetic factors, behaviors, diets, or other conditions or factors. The conditions or factors that lead to elevated cardiovascular risk include, without limitation: systemic lupus erythematosus, current or prior cigarette smoking, diabetes, hemodialysis, receiving an organ transplant, manifest coronary artery disease, history of myocardial infarction, history of transient ischemic attacks or stroke, history of peripheral vascular disease, angina, hypertension, hypercholesterolemia, obesity, atherosclerosis, kidney disease, Chlamydia infection, Bartonella infection, and obstructive pulmonary disease.

The term "cardiovascular event" as used herein refers to a disorder or disease of the cardiovascular system having a rather sudden onset; it can also refer to a rather sudden worsening of such a disorder or disease. Examples of cardiovascular events include, without limitation: cardiac arrest, myocardial infarction, ischemia, stroke, worsening of angina, and congestive heart failure.

II. The Active Agents

A. Cholesterol-Lowering Agents

This invention employs any effective cholesterol-lowering agent or combination of such agents. Preferred cholesterol-lowering agents are HMG CoA reductase inhibitors, bile acid sequestrants, probucol, and fibric acid agents. Particularly preferred are HMG CoA reductase inhibitors, especially atorvastatin, cerivistatin, fluindostatin, fluvastatin, lovastatin, mevastatin, pravastatin, simvastatin, and velostatin; the most preferred agents are lovastatin and pravastatin, particularly lovastatin. Cholesterol-lowering agents are well known in the art and are discussed and reviewed in numerous publications; a useful review is presented by Witztum, J. L., "Drugs used in the treatment of hyperlipidemia", in Hardman, J. G., Gilman, A. G., and Limbird, L. E., editors, Goodman and Gihnan's The Pharmacological Basis of Therapeutics, $9^{th}$ Edition, pp. 875–897 (New York: McGraw-Hill, 1996). Brief descriptions of some of the classes of cholesterol-lowering agents that may be used in this invention follow.

HMG CoA reductase inhibitors: The members of this class of compounds inhibit 3-hydroxy-3-methylglutaryl coenzyme A (HMG CoA) reductase. This enzyme catalyzes the conversion of HMG CoA to mevalonate, which is an early and rate-limiting step in the biosynthesis of cholesterol. Examples of HMG CoA reductase inhibitors that may be used include but are not limited to lovastatin (MEVACOR™; see U.S. Pat. No. 4,231,938), simvastatin (ZOCOR™; see U.S. Pat. No. 4,444,784), pravastatin (PRAVACHOL™; see U.S. Pat. No. 4,346,227), fluvastatin (LESCOL™; see U.S. Pat. No. 5,354,772), atorvastatin (LIPITOR™; see U.S. Pat. No. 5,273,995), cerivastatin (also called rivastatin; see U.S. Pat. No. 5,177,080), mevastatin (see U.S. Pat. No. 3,883140), fluindostatin (Sandoz XU-62-320), velostatin (also called synvinolin; see U.S. Pat. Nos. 4,448,784 and 4,450,171), and compounds related to these as described in the cited references. Some other examples of HMG CoA reductase inhibitors that may be used are, without limitation, presented in U.S. Pat. No. 6,264,938 at Table 1 and U.S. Pat. No. 5,622,985, columns 3 through 6. All pharmaceutically acceptable HMG CoA reductase inhibitors are included in this invention. Compounds that inhibit the activity of HMG CoA reductase can be readily identified by using assays well known in the art; see, as examples, the assays described or cited in U.S. Pat. No. 4,231,938 at column 6, and in International Patent Publication WO 84/02131 at pp. 30–33. The term "HMG CoA reductase inhibitor" is intended to include all pharmaceutically acceptable salt, ester, and lactone forms of compounds that have HMG CoA reductase inhibitory activity, and therefore the use of such salt, ester, and lactone forms is included within the scope of this invention.

HMG CoA reductase inhibitors are particularly preferred cholesterol-lowering agents herein, insofar as they tend to exhibit fewer undesirable side effects than other cholesterol-lowering agents, are more desirable in terms of safety and tolerance issues, do not need to be titrated, and exhibit one or more beneficial effects in addition to lowering cholesterol, e.g., a reduction in bone loss.

Bile acid sequestrants: Bile acids, which are secreted into the intestine to aid in the digestion and absorption of lipids, are synthesized in the liver from cholesterol. Normally, approximately 97% of bile acids are reabsorbed and reused. If large amounts of bile acids are excreted, then the liver must convert more cholesterol to bile acids, lowering serum cholesterol levels, particularly LDL cholesterol levels. Although biosynthesis of cholesterol is up-regulated in this case, the net effect of increased bile acid synthesis in most individuals is to lower cholesterol, particularly LDL cholesterol, levels in the serum.

Bile acid sequestrants are poorly absorbed resins or other substances that bind to and sequester bile acids in the intestine. The sequestered bile acids are subsequently excreted in the feces. Any pharmaceutically acceptable bile acid sequestrant may be used in the practice of this invention. Examples of bile acid sequestrants that may be used in this invention include, without limitation, cholestyramine, colesevelam, colestipol, poly[methyl-(3-trimethylaminopropyl)imino-trimethylene dihalide], and those disclosed in U.S. Pat. No. 6,271,264, International Patent Publication WO 95/34585, and European Patent Specification EP O 622.

Probucol: This compound is a potent lipophilic antioxidant that inhibits the oxidation of LDL cholesterol. As the oxidation of LDL cholesterol may be an important, and perhaps essential, factor in the development of atherosclerotic lesions, probucol may be useful in preventing or treating atherosclerosis. Although probucol is known to lower serum cholesterol levels, the mechanism of action is not well understood. Probucol is often useful in treating patients who do not respond to other cholesterol-lowering drugs, such as patients with homozygous familial hypercholesterolemia.

Fibric acid derivatives: These compounds, also known as "fibrates," lower triglyceride levels, raise high density lipoprotein (HDL) levels, and have variable effects on LDL cholesterol levels in the blood. Examples of fibric acid derivatives that may be used in this invention include, without limitation, bezafibrate (Bezalip™), beclobrate, binifibrate, ciprofibrate, clinofibrate, clofibrate, etofibrate, fenofibrate (Lipidil™ Lipidil Micro™), gemfibrozil (Lopid™), nicofibrate, pirifibrate, ronifibrate, simfibrate, and theofibrate.

B. Inhibitors of the Renin-Angiotensin System

The renin-angiotensin system plays a major role in regulating blood pressure. Renin, an enzyme synthesized, stored, and secreted by the kidneys, potently increases blood pressure; normally, its secretion increases when blood pressure is low and decreases when blood pressure is high. Renin functions by acting on angiotensinogen to form the decapeptide angiotensin I. Angiotensin I is rapidly converted to the octapeptide angiotensin II by angiotensin converting enzyme (ACE). Angiotensin II acts by numerous mechanisms to raise blood pressure, including raising total peripheral resistance (in part by constricting precapillary arterioles and, to a lesser extent, postcapillary venules; by enhancing peripheral noradrenergic neurotransmission; and by central nervous system effects), reducing sodium excretion while increasing potassium excretion by the kidneys, and increasing aldosterone secretion by the adrenal cortex (aldosterone acts to retain sodium and to excrete potassium and hydrogen ions). Angiotensin II is also believed to contribute to pathological structural changes in the cardiovascular system, including cardiac hypertrophy (excessive tissue mass), cardiac fibrosis (associated with congestive heart failure and myocardial infarction), and thickening of the intimal surface of blood vessel walls (associated with atherosclerosis).

Drugs to lower blood pressure have been developed that successfully target several pathways in the renin-angiotensin system. Best known and most widely used are the ACE inhibitors, which inhibit the conversion of angiotensin I to angiotensin II. Also developed are angiotensin II receptor antagonists and renin inhibitors. These classes of drugs are briefly discussed below; much more information is readily available in published literature (see, for example, the review by Jackson, E. K. and Garrison, J. C., in Hardman, J. G., Gilman, A. G., and Limbird, L. E., editors, Goodman and Gilman's The Pharmacological Basis of Therapeutics, 9$^{th}$ Edition, pp. 733–754 (New York: McGraw-Hill, 1996). ACE inhibitors are the preferred inhibitors of the renin-angiotensin system for use in conjunction with the present compositions. It should also be noted that in addition to lowering blood pressure, ACE inhibitors reduce plasma levels of TGF-$\beta$, an added benefit in many patients, e.g., those suffering from systemic lupus erythematosus.

Angiotensin converting enzyme (ACE) inhibitors: As mentioned, ACE inhibitors inhibit the conversion of angiotensin I to angiotensin II. Because angiotensin I has only about 1% of the hypertensive activity of angiotensin II, ACE inhibitors are generally effective in reducing blood pressure and the other adverse cardiovascular effects caused by angiotensin II. ACE has numerous substrates other than angiotensin I, including bradykinin. By interfering with the conversion of bradykinin, ACE inhibitors increase bradykinin levels; this mechanism may contribute to the efficacy of ACE inhibitors.

Also included in this invention are ACE/NEP inhibitors, which are ACE inhibitors that also have an inhibitory effect on neutral endopeptidase (NEP), an enzyme that degrades atrial natriuretic peptide. Inhibition of NEP may be particularly effective in controlling volume-expanded hypertension.

Numerous ACE inhibitors have been synthesized. Most of these compounds can be classified into three groups based on their chemical structure: (1) sulfhydryl-(also called mercapto-) containing ACE inhibitors, including captopril and agents that are structurally related to captopril, such as fentiapril, pivalopril, zofenopril and alacepril; (2) dicarboxyl-containing ACE inhibitors, including enalapril and agents that are structurally related to enalapril, such as lisinopril, benazepril, quinapril, moexipril, ramipril, spirapril, perindopril, indolapril, pentopril, indalapril and cilazapril; and (3) phosphorus-containing ACE inhibitors, structurally related to fosinopril. Many of the ACE inhibitors are esters developed for high oral bioavailability, but with low potency in themselves; they must be converted to particular metabolites in the body that have potent activity.

ACE inhibitors are well known in the art, and the use of any pharmaceutically acceptable ACE inhibitor, including any of those mentioned in the preceding paragraph, is included in this invention, including mixtures thereof and/or their pharmaceutically acceptable salts. Some further examples of ACE inhibitors that may be used in the practice of this invention are, without limitation, AB-103, ancovenin, benazeprilat, BRL-36378, BW-A575C, CGS13928C, CL242817, CV-5975, Equaten, EU-4865, EU-4867, EU-5476, foroxymithine, FPL 66564, FR-900456, Hoe-065, 15B2, indolapril, ketomethylureas, KRI-1177, KRI-1230, L681176, libenzapril, MCD, MDL-27088, MDL-27467A, moveltipril, MS-41, nicotianamine, pentopril, phenacein, pivopril, rentiapril, RG-5975, RG-6134, RG-6207, RGH0399, ROO-911, RS-10085-197, RS-2039, RS 5139, RS-86127, RU-44403, S-8308, SA-291, spiraprilat, SQ26900, SQ-28084, SQ-28370, SQ-28940, SQ-31440, Synecor, utibapril, WF-10129, Wy-44221, Wy-44655, Y23785, Yissum, P-0154, zabicipril, Asahi Brewery AB-47, alatriopril, BMS 182657, Asahi Chemical C-111, Asahi Chemical C-112, Dainippon DU-1777, mixanpril, Prentyl, zofenoprilat, 1(-(I-carboxy-6-(4-piperidinyl)hexyl)amino)- 1-oxopropyl octahydro-IH-indole-2-carboxylic acid, Bioproject BP1.137, Chiesi CHF 1514, Fisons FPL-66564, idrapril, perindoprilat, Servier S-5590, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat, spirapril, and those listed in U.S. Pat. No. 6,248,729.

Preferred ACE inhibitors are captopril, cilazapril, delapril, enalapril, fentiapril, fosinopril, indolapril, lisinopril, perindopril, pivopril, quinapril, ramipril, spirapril, trandolapril, and zofenopril; particularly preferred are captopril, enalapril, fosinopril, lisinopril, quinapril, ramipril, and trandolapril; and most preferred is enalapril.

Some examples of ACE/NEP inhibitors for use herein include, without limitation, those disclosed in U.S. Pat. Nos. 5,508,272, 5,362,727, 5,366,973, 5,225,401, 4,722,810, 5,223,516, 5,552,397, 4,749,688, 5,504,080, 5,612,359, and 5,525,723, and European Patent Applications 0481,522, 0534363A2, 534,396, and 534,492. Preferred are those ACE/NEP inhibitors that are designated as preferred in the above U.S. patents. Particularly preferred are the ACE/NEP inhibitors omapatrilat (disclosed in U.S. Pat. No. 5,508,272) and MDL100240 (disclosed in U.S. Pat. No. 5,430,145).

Angiotensin II receptor antagonists (also known as angiotensin II antagonists): Angiotensin II binds to angiotensin subtype 1 ($AT_1$) and subtype 2 ($AT_2$) receptors, as well as to several other receptors. All the known physiological effects of angiotensin II are apparently due to its binding to, and activation of, the $AT_1$ receptor, which is abundantly expressed in the tissues affected by angiotensin II. $AT_2$ receptor is common in some fetal tissues but is scarce in adult tissues; to date, no known function has been discovered for it. Many orally active, nonpeptide angiotensin II receptor antagonists have been developed. Most of these are directed at the $AT_1$ receptor, but due to concerns about unbalanced activation of the $AT_2$ receptor, some newer angiotensin II receptor antagonists target both $AT_1$, and $AT_2$ receptors. Angiotensin II receptor antagonists are generally highly specific, having very little effect on other hormone receptors or ion channels.

Any orally active antagonists of the $AT_1$, angiotensin II receptor may be used in this invention. Some examples of angiotensin II receptor antagonists suitable for use herein are saralasin (including saralasin acetate), candesartan (including candesartan cilexetil), CGP-63170, EMD-66397, KT3-671, LRB/081, valsartan, A-81282, BIBR-363, BIBS-222, BMS-184698, CV11194, EXP-3174, KW-3433, L-161177, L-162154, LR-B/057, LY-235656, PD150304, U-96849, U-97018, UP-275-22, WAY-126227, WK-1492.2K, YM-31472, losartan (including losartan potassium), E-4177, EMD-73495, eprosartan, HN-65021, irbesartan, L-159282, ME-3221, SL-91.0102, tasosartan, telmisartan, UP-269-6, YM-358, CGP-49870, GA-0056, L-159689, L-162234, L-162441, L-163007, PD-123177, A81988, BMS-180560, CGP-38560A, CGP-48369, DA-2079, DE-3489, DuP-167, EXP-063, EXP-6155, EXP-6803, EXP-7711, EXP-9270, FK-739, HR-720, ICI D6888, ICI-D7155, ICI-D8731, isoteoline, KRI-1177, L-158809, L-158978, L-159874, LR B087, LY-285434, LY-302289, LY-315995, RG-13647, RWJ-38970, RWJ-46458, S-8307, S-8308, saprisartan, sarmesin, WK-1360, X-6803, ZD-6888, ZD-7155, ZD-8731, BIBS39, CI-996, DMP-811, DuP-532, EXP-929, L163017, LY-301875, XH-148, XR-510, zolasartan, and PD-123319.

Preferred angiotensin II receptor antagonists include losartan (which is the prototype and best known angiotensin II receptor antagonist), irbesartan, eprosartan, candesartan, valsartan, telmisartan, zolasartin, and tasosartan. Particularly preferred is losartan.

Renin inhibitors: Compounds that inhibit renin activity include: renin antibodies; analogs of the prosegment of renin; analogs of pepstatin; and analogs of the renin substrate angiotensinogen. As most of these compounds are peptides, they tend to have low oral bioavailability. Non-peptide renin inhibitors are of most interest in this invention. Preferred renin inhibitors are remikiren (Ro 42-5892), A-72517, and A-74273, with remikiren being most preferred.

C. Aspirin

Aspirin (acetylsalicylic acid), when administered in low daily doses over a long term to patients at risk for cardiovascular events, is well established to prevent myocardial infarction and strokes due to thrombosis. Second heart attacks, strokes, and cardiovascular deaths are reduced by at least 25% through the daily administration of low doses (approximately 80 mg) of aspirin.

A number of mechanisms are likely responsible for the cardiovascular protective activity of aspirin, but its antithrombotic, anti-platelet aggregating activities are probably highly significant in this regard. Aspirin irreversibly acetylates the enzyme cyclooxygenase, rendering it nonfunctional. Cyclooxygenase is essential to the synthesis of (among other compounds) prostaglandins, many of which are proinflammatory; thromboxane $A_2$, which is synthesized by platelets to promote platelet aggregation and ultimately thrombosis (blood clotting); and prostacyclins, which have anti-platelet aggregating properties. Cyclooxygenases are synthesized in endothelial cells and not in platelets. Low doses of aspirin neutralize cyclooxygenase selectively in the platelets, while allowing continued cyclooxygenase and prostacyclin synthesis in the endothelial cells. The net effect is to reduce inflammation and platelet aggregation, and thus thrombosis, in the blood vessels.

While aspirin is most preferred for use in this invention, other salicylates, including magnesium salicylate, and other anti-platelet aggregating agents, such as anagrelide, dipyridamole, clopidogrel, and ticlopidine, may also be used herein. Other cyclooxygenase inhibitors, including other nonsteroidal anti-inflammatory drugs (NSAIDS) such as ibuprofen, sulindac, sulindac sulfide, sulindac sulfone, flurbiprofen, indomethacin, naproxen, meclafenamic acid, and piroxicam, may also be used in this invention.

D. Vitamin B Compounds

Elevated serum levels of homocysteine, an amino acid not found in proteins, is highly correlated with atherosclerosis, heart disease, stroke, and peripheral vascular disease. Many studies have shown that orally administered supplements of vitamin $B_6$ (also called pyridoxine), vitamin $B_{12}$ (also called cyanocobalamin), and folic acid (or folates) can lower homocysteine levels and reduce the incidence of atherosclerosis, myocardial infarction, and stroke. Folic acid and folates appear particularly potent in this regard. Recent surveys have found that approximately 88% of Americans have a daily intake of folic acid that is below the 400 micrograms per day that is recommended to maintain normal homocysteine levels. In the practice of this invention, folinic acid or folates may be used instead of folic acid, though folic acid is preferred. Folates that may be used include 5-methyl tetrahydrofolic acid (5MeTHF), tetrahydrofolic acid (THF), and 5-formyl tetrahydrofolic acid (5CHOTHF).

E. Derivatives

Any of the active agents may be administered in the form of a salt, ester, amide, prodrug, active metabolite, analog, or the like, provided that the salt, ester, amide, prodrug, active metabolite, or analog is pharmaceutically acceptable and pharmacologically active in the present context. Salts, esters, amides, prodrugs, metabolites, analogs, and other derivatives of the active agents may be prepared using standard procedures known to those skilled in the art of synthetic organic chemistry and described, for example, by J. March, Advanced Organic Chemistry: Reactions, Mechanisms and Structure, 4th Edition (New York: Wiley-Interscience, 1992).

For example, acid addition salts are prepared from a drug in the form of a free base using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties that may be present on an active agent may be carried out in a similar manner using a pharmaceutically acceptable base such as sodium hydroxide, potassium hydroxide, ammonium hydroxide, calcium hydroxide, trimethylamine, or the like. Preparation of esters involves transformation of a carboxylic acid group via a conventional esterification reaction involving nucleophilic attack of an $RO^-$ moiety at the carbonyl carbon. Esterification may also be carried out by reaction of a hydroxyl group with an esterification reagent such as an acid chloride. Esters can be reconverted to the free acids, if desired, by using conventional hydrogenolysis or hydrolysis procedures. Amides may be prepared from esters, using suitable amine reactants, or they may be prepared from an anhydride or an acid chloride by reaction with ammonia or a lower alkyl amine. Prodrugs and active metabolites may also be prepared using techniques known to those skilled in the art or described in the pertinent literature. Prodrugs are typically prepared by covalent attachment of a moiety that results in a compound that is therapeutically inactive until modified by an individual's metabolic system.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

III. Pharmaceutical Compositions and Dosage Forms

When two or more active agents are combined in a single pharmaceutical dosage form, possible interactions among the active agents, and among the active agents and the excipients, must be considered. Such consideration is well within the purview of those skilled in the art of pharmaceutical formulation. For example, aspirin is acidic and may react with basic compounds or alkali esters in such a way as to cause hydrolysis of the aspirin and/or degradation of the other compounds. Aspirin may, for example, react with acid labile compounds such as pravastatin to degrade them. The present composition thus encompasses pharmaceutical compositions wherein two or more of the active agents are separated from each other within the pharmaceutical dosage form, by, for example, separating potentially interacting compounds from each other within the pharmaceutical dosage form, as in separate flat layers of a tablet (e.g., a bilayer or trilayer tablet), concentric layers, coated beads or granules (which may be incorporated into a compressed tablet or into a capsule), and/or by using buffers (see, for example, U.S. Pat. No. 6,235,311). It will also be appreciated by those in the art that such dosage forms, wherein two or more active agents are physically separated from the other active agents, can be manufactured so that different active agents will have different release profiles, e.g., if one active agent is formulated with an enteric coating, another active agent is formulated in a sustained release matrix, and the like. Alternatively, non-reactive pharmaceutically active derivatives of one or more of the potentially interacting compounds may be used, such as using a neutral salicylate instead of aspirin.

The invention provides pharmaceutical dosage forms that contain two or more multiple dosage units that are physically segregated from each other, wherein the various dosage units may have different release profiles. For example, one or more dosage units may provide immediate release of an active agent (e.g., within about an hour following oral ingestion), one or more dosage units may provide sustained release of an active agent (such that the active agent therein is gradually released over an extended time period), and one or more dosage units may provide delayed release of an active agent, wherein release following the initial "delay" may or may not be sustained release. Drug release may be made "pulsatile" in that two or more drug doses are released at spaced apart intervals of time.

In one embodiment, the dosage forms are closed and preferably sealed capsules housing at least two drug-containing dosage units wherein each dosage unit within the capsule may or may not provide a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In another embodiment, the individual dosage units are compacted in a single tablet, and may represent integral but discrete segments thereof (e.g., layers) or be present in an admixture. Layered tablets, with each layer containing a different active agent and/or providing a different release profile, provide several manufacturing advantages. Such tablets may be made in single step compression, thereby eliminating the operations of methods necessary for preparing coated core dosage forms. Layered tablets additionally eliminate the concomitant steps of in-process and quality controls for manufacturing two or more different tablets. Further, layers containing only excipients can be interspersed between layers that contain active agents, to prevent possible interactions between or among the active agents. With tablets containing different dosage units in admixture, drug-containing beads, granules or particles with different drug release profiles (e.g., immediate and delayed release profiles), and/or drug-containing beads, granules or particles containing different active agents, can be compressed together into a single tablet using conventional tableting means. In the admixture, there is a random possibility of the different active agents coming into contact with each other. However, protective and/or delayed release coatings provided on the granules or other dosage units provide a physical barrier, thereby minimizing direct physical contact between the active agents.

In still another embodiment, a dosage form of the invention comprises a coated core-type delivery system wherein an outer layer is comprised of one active agent, one or more intermediate layers are optionally present each containing one or more additional active agents, and an internal core contains still another active agent, or is comprised of an inert material. Each layer and/or the core may also provide different release profiles.

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily a incorporating a polymeric material; increasing drug particle size; placing the drug within a matrix; and forming complexes of the drug with a suitable complexing agent.

Delayed Release Dosage Units and Enteric Coatings: Solid dosage forms, whether tablets, capsules, caplets, or particulates, may, if desired, be coated so as to provide for delayed release. Dosage forms with delayed release coatings may be manufactured using standard coating procedures and equipment. Such procedures are known to those skilled in the art and described in the pertinent texts, e.g., in Remington, supra. Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

The delayed release dosage units in any of the embodiments of the invention can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials are comprised of bioerodible, gradually hydrolyzable, gradually water-soluble, and/or enzymatically degradable polymers, and preferred delayed release coatings are comprised of enteric coating materials.

Enteric coating compositions generally comprise a polymeric material that, following oral administration of a dosage form to a patient, prevents release of the active agent until the small intestine of the patient is reached. Generally, this requires that the polymeric material—i.e., the enteric polymer—prevent drug release in the acidic environment of the stomach but dissolve sufficiently in the small intestines to gradually release the active agent therein. The enteric coating material, therefore, should not dissolve in gastrointestinal fluids at a pH below about 4 or 5, but should ionize and thus does dissolve at a pH of about 5 and above. Accordingly, among the most effective enteric coating materials are polyacids having a $pK_a$ in the range of about 3 to 5, although it is expected that any material exhibiting the aforementioned pH-dependent solubility profile can be used as an enteric coating in the practice of the present invention to achieve delivery of an active agent to the lower gastrointestinal tract. The selection of the specific enteric coating material will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; ease of application as a coating; and economical practicality.

An enteric coating also prevents exposure of an active agent to the epithelial and mucosal tissue of the buccal cavity, pharynx, esophagus, and stomach, and to the enzymes associated with these tissues. The enteric coating therefore helps to protect the active agent and a patient's internal tissue from any adverse event prior to drug release at the desired site of delivery.

The "coating weight", or relative amount of coating material per dosage unit, generally dictates the time interval between ingestion and drug release. The preferred coating weights for particular coating materials may be readily determined by those skilled in the art by evaluating individual release profiles for tablets, beads and granules prepared with different quantities of various coating materials. Generally, however, coating weights of approximately 5 wt. % to 50 wt. % are appropriate.

Suitable enteric polymers include, but are not limited to, polymerized gelatin, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), shellac, zein, and acrylic acid polymers and copolymers, preferably formed from acrylic acid, methacrylic acid, methyl acrylate, ethyl acrylate, methyl methacrylate, ethyl methacrylate, and/or other vinyl monomers. Preferred enteric polymers are acrylic acid and methacrylic acid polymers and copolymers, particularly those that are commercially available under the tradenames Eudragit® L and Eudragit® S, in which the ratio of free carboxyl to ester groups is approximately 1:1 and 1:2, respectively, and wherein each copolymer has a (weight average) molecular weight of approximately 135,000 Da.

The coating can, and usually does, contain a plasticizer to prevent the formation of pores and cracks that would permit the penetration of the gastric fluids. Suitable plasticizers include, but are not limited to, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

Enterically coated dosage forms, whether enterically coated tablets, tablet segments, capsules, granules, or beads, may be manufactured using standard enteric coating procedures and equipment. For example, an enteric coating can be applied to a tablet, tablet segment, bead, granule, caplet or capsule using a coating pan, an airless spray technique, fluidized bed coating equipment, or the like. Detailed information concerning materials, equipment and processes for preparing coated dosage forms may be found in *Pharmaceutical Dosage Forms: Tablets,* eds. Lieberman et al. (New York: Marcel Dekker, Inc., 1989), and in Ansel et al., *Pharmaceutical Dosage Forms and Drug Delivery Systems,* $6^{th}$ Ed. (Media, Pa.: Williams & Wilkins, 1995). The coating thickness, as noted above, must be sufficient to ensure that the oral dosage form remains intact until the desired site of delivery in the lower intestinal tract is reached.

Alternatively, a delayed release dosage unit may be formulated by dispersing an active agent within a matrix of a suitable material such as an enteric coating material or other delayed release polymeric materials. Hydrophilic polymers and certain fatty compounds are particularly useful for providing a delayed release matrix. Such hydrophilic polymers may be comprised of polymers or copolymers of cellulose, cellulose ester, acrylic acid, methacrylic acid, methyl acrylate, ethyl acrylate, and vinyl or enzymatically degradable polymers or copolymers as described above. Fatty compounds for use as a matrix material include, but are not limited to, waxes (e.g. carnauba wax) and glycerol tristearate. Once the active ingredient is mixed with the matrix material, the mixture can be compressed into tablets.

Immediate Release Dosage Units: The immediate release dosage unit of the present dosage forms—i.e., a tablet within a capsule, a plurality of drug-containing beads, granules or particles, a layer within a multilayered tablet, or a layer or core of a coated core dosage form—contains a therapeutically effective quantity of a particular active agent or mixture of active agents, with conventional pharmaceutical excipients. The immediate release dosage units may or may not be coated with a protective coating. A preferred method for preparing immediate release tablets (e.g., as incorporated into a capsule) is by compressing a drug-containing blend, e.g., blend of granules, prepared using a direct blend, wet-granulation or dry-granulation process. Immediate release tablets may also be molded rather than compressed, starting with a moist material containing a suitable water-soluble lubricant. However, preferred tablets herein are manufactured using compression rather than molding. A preferred method for forming an immediate release drug-containing blend is to mix drug particles directly with one or more excipients such as diluents (or fillers), binders, disintegrants, lubricants, glidants, colorants or the like. Beads containing the active agent in immediate release form may also be prepared by any one of a number of conventional techniques, typically starting from a fluid dispersion. For example, a typical method for preparing drug-containing beads involves blending the active agent with conventional pharmaceutical excipients such as microcrystalline cellulose, starch, polyvinylpyrrolidone, methylcellulose, talc, metallic stearates, silicone dioxide, or the like. The admixture is used to coat a bead core such as a sugar sphere (or so-called "non-pareil") having a size of approximately 20 to 60 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

Sustained release dosage forms and dosage units: Sustained release formulations provide for drug release over an extended time period, and may or may not be delayed release. Generally, as will be appreciated by those of ordinary skill in the art, sustained release dosage units are formulated by dispersing a drug within a matrix of a gradually bioerodible (hydrolyzable) material such as an insoluble plastic, a hydrophilic polymer, or a fatty compound, or by coating a solid, drug-containing dosage form with such a material. Insoluble plastic matrices may be comprised of, for example, polyvinyl chloride or polyethylene.

Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, particularly those commercially available under the tradename Eudragit®, with a terpolymer of ethyl acrylate, methyl methacrylate and trimethylammonioethyl methacrylate chloride (sold under the tradename Eudragit® RS) representing one preferred example; vinyl polymers and copolymers such as polyvinyl pyrrolidone, polyvinyl acetate, polyvinylacetate phthalate, vinylacetate crotonic acid copolymer, ethylene-vinyl acetate copolymers, and polyvinyl acetate/polyvinyl pyrrolidone mixtures; carbomers, i.e., hydroxylated vinylic polymers referred to as "interpolymers," which are prepared by crosslinking a monoolefinic acrylic acid monomer with a polyalkyl ether of sucrose (available under the tradename Carbopol® from the B. F. Goodrich Chemical Company); zein; and shellac, ammoniated shellac, shellac-acetyl alcohol, and shellac n-butyl stearate.

Fatty compounds for use as a sustained release matrix material or as a sustained release coating material include, but are not limited to, waxes generally (e.g., carnauba wax), glyceryl tristearate, and hydrogenated oils such as hydrogenated vegetable oil, cottonseed oil, castor oil, canola oil, palm oil, palm kernel oil and soybean oil.

Protective Coatings: Any of the dosage forms of the invention, and any of the dosage units contained therein, may be coated with a protective coating. If a delayed release or sustained release coating is also used, the protective coating is applied thereover. Suitable protective coating materials will be known to those of ordinary skill in the art and are described in the pertinent texts, e.g., Remington's, supra. Generally, however, protective coatings are comprised of a material that serves as a sealant encasing the individual dosage units, such that the different active agents are physically isolated from each other within the dosage form. Coating materials suitable as sealants are generally comprised of a resinous material such as shellac, zein, cellulose acetate phthalate, polyvinyl acetate phthalate, or a shellac-polyvinylpyrrolidone combination. Sealant coatings may also be applied to the outer surface of an entire dosage form, to strengthen a tablet or capsule and improve product stability.

Dosageform manufacture: Tablets may be manufactured using standard tablet processing procedures and equipment. One method for forming tablets is by direct compression of a powdered, crystalline, or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In addition to the active agent(s), then, tablets prepared for oral administration using the method of the invention will generally contain other materials such as binders, diluents, lubricants, disintegrants, fillers, stabilizers, surfactants, coloring agents, and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch, and powdered sugar. Lubricants are used to facilitate tablet manufacture; examples of suitable lubricants include, for example, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers are used to inhibit or retard drug decomposition reactions that include, by way of example, oxidative reactions. Surfactants may be anionic, cationic, amphoteric, or nonionic surface-active agents.

The dosage form may also be a capsule, in which case the active agent-containing composition may be encapsulated in the form of a liquid or solid (including particulates such as granules, beads, powders, or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: *The Science and Practice of Pharmacy,* cited supra, which describes materials and methods for preparing encapsulated pharmaceuticals. If the active agent-containing composition is present within the capsule in liquid form, a liquid carrier is necessary to dissolve the active agent(s). The carrier must be compatible with the capsule material and all components of the pharmaceutical composition, and must be suitable for ingestion.

In one embodiment, then, the cholesterol-lowering agent, the inhibitor of the renin-angiotensin system, and the aspirin are each individually contained within a separate layer of a multilayered tablet (said tablet herein designated "Tablet ML1"). Tablet ML1 may further comprise a layer of excipient, preferably microcrystalline cellulose, between the layers containing aspirin and the layer(s) containing the other active agents. Additionally, Tablet ML1 may include a layer that contains at least one of vitamin $B_6$, vitamin $B_{12}$, and folate. Preferably, a single layer contains vitamin $B_6$, vitamin $B_{12}$, and folate blended together. In a particularly preferred embodiment, the cholesterol-lowering agent, the inhibitor of the renin-angiotensin system, and the aspirin are each individually contained within a separate layer of a multilayered tablet in unit doses appropriate for once-daily dosing, further wherein the cholesterol-lowering agent and the inhibitor of the renin-angiotensin system are each in a controlled release dosage unit (e.g., a sustained release and/or delayed release dosage unit) and the aspirin is in an immediate release dosage unit (said tablet herein designated "Tablet ML2"). In a particularly preferred embodiment, Tablet ML2 further comprises a layer that comprises vitamin $B_6$, vitamin $B_{12}$, and folate blended together (said tablet herein designated "Tablet ML3"). In a highly preferred embodiment, Tablet ML3 comprises 80 mg lovastatin as the cholesterol-lowering agent, 40 mg enalapril as the inhibitor of the renin-angiotensin system, 81 mg aspirin, 50 mg vitamin $B_6$, 1 mg vitamin $B_{12}$, and 3 mg folic acid.

In another embodiment, wherein the dosage form of the invention comprises a table containing active agent beads in a blended matrix, at least one of the active agents is formulated into beads and at least one of the other active agents is formulated into the matrix of the tablet that surrounds the beads. The beads may be uncoated, be coated with a protective layer, be enterically coated, be coated or otherwise formulated for sustained released, or be coated or otherwise formulated for delayed release. The matrix may be formulated for immediate release, delayed release, or sustained release. In a preferred embodiment, the cholesterol-lowering agent and the inhibitor of the renin-angiotensin system are each individually formulated into a plurality of beads, said beads being formulated for sustained release, while the aspirin is comprised within the matrix, said matrix being formulated for immediate release (said tablet herein designated "Tablet B1"). In a particularly preferred embodiment, Tablet B1 further comprises vitamin $B_6$, vitamin $B_{12}$, and folate blended together with the aspirin in the matrix, and each of the active agents is present in a unit dosage appropriate for once-daily dosing (said tablet herein designated "Tablet B2"). In a highly preferred embodiment, Tablet B2 comprises 80 mg lovastatin as the cholesterol-lowering agent, 40 mg enalapril as the inhibitor of the renin-angiotensin system, 81 mg aspirin, 50 mg vitamin $B_6$, 1 mg vitamin $B_{12}$, and 3 mg folic acid.

In a further embodiment, wherein the dosage form of the invention comprises blended immediate release tablets or capsules, all the active agents are blended together as one dosage unit in one immediate release dosage form, either a tablet or a capsule. In this embodiment, care is taken to ensure the stability and compatibility of the active agents; appropriate buffers and other excipients are used, when necessary, to help ensure said stability and compatibility. In a preferred embodiment, the tablet or capsule comprises 80 mg lovastatin as the cholesterol-lowering agent, 40 mg enalapril as the inhibitor of the renin-angiotensin system, 81 mg aspirin, 50 mg vitamin $B_6$, 1 mg vitamin $B_{12}$, and 3 mg folic acid. In a particularly preferred embodiment, each of the six active agents is individually formulated into a plurality of protectively coated beads or granules, the coating serving to prevent or inhibit chemical interaction among the active agents.

In a further embodiment, wherein the dosage form of the invention is comprised of coated beads or granules in a tablet or capsule, each active agent is individually formulated into a plurality of coated beads or granules, the coating serving to prevent or inhibit chemical interaction among the active agents and, optionally, serving to sustain or delay release of the active agent. In a preferred embodiment, the cholesterol-lowering agent and the inhibitor of the renin-angiotensin system are each formulated into beads or granules coated and otherwise formulated for sustained release, while the aspirin is formulated into beads or granules coated and otherwise formulated for immediate release (said tablet or capsule designated herein as "Tablet or Capsule CBG1"). In a particularly preferred embodiment, Tablet or Capsule CBG1 further comprises vitamin $B_6$, vitamin $B_{12}$, and folate each individually formulated into beads or granules for immediate release, and each of the active agents is present in a unit dosage appropriate for once-daily dosing (said tablet or capsule herein designated "Tablet or Capsule CGB2"). In a highly preferred embodiment, Tablet or Capsule CBG2 comprises 80 mg lovastatin as the cholesterol-lowering agent, 40 mg enalapril as the inhibitor of the renin-angiotensin system, 81 mg aspirin, 50 mg vitamin $B_6$, 1 mg vitamin $B_{12}$, and 3 mg folic acid.

In related embodiment, a capsule, preferably a hard gelatin capsule that is preferably sealed, comprises within the interior of the capsule compressed or molded tablets, beads, or granules, plus a pharmaceutically acceptable carrier. Each active agent is individually formulated into a tablet, a plurality of tablets, a plurality of beads, or a plurality of granules. The tablets, beads, or granules may be coated and/or otherwise formulated for immediate release, delayed release, or sustained release. The capsule may contain a mixture of tablets, beads, or granules; further, the capsule may contain a mixture of said dosage units in coated and uncoated forms. A preferred dosage form is a hard, sealed gelatin capsule comprising a cholesterol-lowering agent and an inhibitor of the renin-angiotensin system each individually formulated in a tablet, a plurality of tablets, a plurality of beads, or a plurality of granules formulated for sustained release, plus aspirin, vitamin $B_6$, vitamin $B_{12}$, and folate each individually formulated into a tablet, a plurality of tablets, a plurality of beads, or a plurality of granules formulated for immediate release.

IV. Utility and Administration

The methods and compositions of this invention are directed at individuals who are at elevated cardiovascular risk, where cardiovascular risk comprises the potential for cardiac arrest, acute or chronic myocardial infarction, coronary heart disease, ischemia, stroke, peripheral vascular disease, claudication, worsening angina, restenosis, and/or atherosclerosis. Individuals who are at elevated cardiovascular risk include those with systemic lupus erythematosus; diabetes; angina pectoris; manifest coronary artery disease; hypertension; hypercholesterolemia; kidney disease; Chlamydia infection; Bartonella infection; obstructive pulmonary disease; who are on hemodialysis; who have received an organ transplant; who are obese; who are elderly; who have a family history of heart disease, atherosclerosis, or stroke; who are or have been cigarette smokers; or who have a history of myocardial infarction, transient ischemic attacks, stroke, atherosclerosis, or peripheral vascular disease. The pharmaceutical composition of the invention may also be administered to a patient suffering an acute myocardial infarction (MI) at the time of the MI or immediately thereafter. The compositions of the invention, when administered in this manner, are particularly useful for increasing the likelihood that a patient suffering an acute MI will survive the event.

Many individuals who are at elevated cardiovascular risk are not treated for this condition, commonly due to the lack of an effective, safe, and convenient therapy. For example, women with systemic lupus erythematosus are at increased risk of myocardial infarction and stroke, likely due to an increased propensity for premature atherosclerosis, but are rarely treated adequately to reduce this risk. As therapy would be chronic for individuals at elevated cardiovascular risk, probably for the life of the patient, it should be simple and convenient for the patient. A high compliance rate for chronic therapy is found when a drug is administered orally once per day, preferably at bedtime. The present invention provides a combination of cholesterol-lowering agent, inhibitor of the renin-angiotensin system, aspirin, and optionally B vitamins comprised within a single unit-dose tablet or capsule for once-daily dosing, preferably at bedtime. The present invention thus addresses a major medical need by providing an effective, safe, simple, and convenient way to reduce the risk of cardiovascular events in patients at elevated cardiovascular risk. Such a dosage form provides convenience and simplicity for the patient, thus increasing the chances for patient compliance, especially in patients who already take multiple medications due to existing heart disease or other diseases.

Since three or more active agents are being used together in a combination therapy, the potency of each of the agents and the interactive effects achieved by combining them together must be taken into account. A consideration of these factors is well within the purview of the ordinarily skilled clinician for the purpose of determining the therapeutically effective or prophylactically effective dosage amounts.

Preferred oral dosage forms contain a therapeutically effective unit dose of each active agent, wherein the unit dose is suitable for once-daily oral administration. The therapeutically effective unit dose of any particular active agent will depend, of course, on the active agent, the needs of the patient, and on other factors known to the prescribing physician. Those of ordinary skill in the art of pharmaceutical formulation can readily deduce suitable unit doses for various active agents. In general, however, the therapeutically effective unit dosages for each of the active agents are as follows:

Approximately 10 mg to approximately 120 mg, preferably approximately 25 mg to approximately 90 mg, of an HMG CoA reductase inhibitor selected from the group consisting of atorvastatin, fluvastatin, lovastatin, pravastatin, and simvastatin.

Approximately 1 mg to approximately 60 mg, preferably approximately 15 mg to approximately 45 mg, of an ACE inhibitor selected from the group consisting of captopril, enalapril, fosinopril, lisinopril, quinapril, ramipril, and trandolapril.

Approximately 20 mg to approximately 600 mg, preferably approximately 20 mg to approximately 150 mg, of aspirin.

Optionally, at least one of:

Approximately 25 mg to approximately 75 mg, preferably approximately 40 mg to approximately 60 mg, of vitamin $B_6$.

Approximately 0.25 mg to approximately 2 mg, preferably approximately 0.5 mg to approximately 1.5 mg, of vitamin $B_{12}$.

Approximately 0.5 mg to approximately 8 mg, preferably approximately 1.5 mg to approximately 5 mg, of folic acid.

In a particularly preferred embodiment, the active ingredients are as follows:

80 mg of lovastatin 40 mg of enalapril 81 mg of aspirin 50 mg of vitamin $B_6$ 1 mg of vitamin $B_{12}$ 3 mg of folic acid The formulations of the invention will be administered for as long as the patient is at elevated cardiovascular risk; very likely, this will be for a prolonged period and possibly for the life of the patient. Administration for a least one to two weeks is required for minimal benefit to be achieved. In addition to the preferred formulations designed for daily dosing, sustained release forms of such formulations may be employed, which may provide for dosing biweekly, weekly, monthly, or the like.

V. Packaged Kits

In another embodiment, a packaged kit is provided that contains a plurality of oral dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the oral dosage forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

It is to be understood that while the invention has been described in conjunction with the preferred specific embodiments thereof, that the foregoing description as well as the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

Experimental

The practice of the present invention will employ, unless otherwise indicated, conventional techniques of pharmaceutical formulation and the like, which are within the skill of the art. Such techniques are fully explained in the literature. In the following examples, efforts have been made to ensure accuracy with respect to numbers used (e.g., amounts, temperatures, etc.) but some experimental error and deviation should be accounted for. Unless otherwise indicated, temperature is in degrees Celsius and pressure is at or near atmospheric pressure at sea level. All reagents were obtained commercially unless otherwise indicated.

EXAMPLE 1

A multilayered tablet comprising one layer of sustained release lovastatin, one layer of sustained release enalapril, and one layer comprising immediate release aspirin, vitamin $B_6$, vitamin $B_{12}$, and folic acid blended together, is prepared as follows. The ingredients of each layer are blended separately, and then compressed to produce a layered tablet using a suitable layered press.

| Ingredient | Mg per Tablet |
| --- | --- |
| Layer 1 (sustained release) | |
| Lovastatin | 80.0 |
| Methocel E4M Premium* | 80.0 |
| Microcrystalline Cellulose | 50.0 |
| Silicon Dioxide | 2.0 |
| Magnesium Stearate | 2.0 |
| Layer 2 (sustained release) | |
| Enalapril | 40.0 |
| Methocel E4M Premium* | 40.0 |
| Microcrystalline Cellulose | 25.0 |
| Silicon Dioxide | 1.0 |
| Magnesium Stearate | 1.0 |
| Layer 3 (excipient barrier) | |
| Microcrystalline cellulose | 25.0 |
| Layer 4 (immediate release) | |
| Aspirin | 81.0 |
| Vitamin $B_6$ | 50.0 |
| Vitamin $B_{12}$ | 1.0 |
| Folic acid | 3.0 |
| Microcrystalline Cellulose | 90.0 |
| Silicon Dioxide | 2.0 |
| Magnesium Stearate | 8.0 |

*Brand of hydroxypropyl methylcellulose available from The Dow Chemical Company, Midland, Michigan.

EXAMPLE 2

Tablets comprising sustained release beads of lovastatin and enalapril in a blended matrix comprising aspirin, vitamin $B_6$, vitamin $B_{12}$, and folic acid are prepared as follows.

| Ingredient | Weight |
| --- | --- |
| Sustained release beads 1 | |
| Lovastatin | 1,000 gm |
| Hydrogenated castor oil | 350 gm |
| Stearic acid | 350 gm |
| Microcrystalline cellulose | 300 gm |
| Total | 2,000 gm |
| Sustained release beads 2 | |
| Enalapril | 1,000 gm |
| Hydrogenated castor oil | 350 gm |
| Stearic acid | 350 gm |
| Microcrystalline cellulose | 300 gm |
| Total | 2,000 gm |
| Immediate release matrix | |
| Aspirin | 810 gm |
| Vitamin $B_6$ | 500 gm |
| Vitamin $B_{12}$ | 10 gm |
| Folic acid | 30 gm |
| Microcrystalline Cellulose | 950 gm |
| Silicon Dioxide | 20 gm |
| Magnesium Stearate | 80 gm |
| Total | 2400 gm |

The powdered ingredients of each of the bead formulations and of the matrix layer are blended separately. To make each of the bead formulations, purified water (700 gm) is added to the powder of the above components, and the mixture is kneaded and extruded from an extrusion granulator to obtain rod-shaped granules. The granules are then rounded by a Marumerizer and dried at 55 degrees Celsius for 3 hours. Beads thus prepared are sieved to obtain sustained release beads that pass through a 14 mesh sieve but not a 26 mesh sieve. The sustained-release beads are then blended with the matrix formulation and compress-molded to tablets. The sustained release beads and the matrix are blended and then compressed into tablets to produce the following composition per tablet:

80 mg of lovastatin
40 mg of enalapril
81 mg of aspirin
50 mg of vitamin $B_6$
1 mg of vitamin $B_{12}$
3 mg of folic acid

EXAMPLE 3

Tablets are prepared as in Example 2, except that the sustained release beads are all coated with an enteric polymer in an aqueous or non-aqueous system. The sustained release beads for lovastatin and enalapril are coated separately. Eudragit L-30D-55 containing 10%–15% of diethyl phthalate (w/w) is used in an aqueous system. The coating suspension is prepared having solid contents of 10%–30%. To prepare the coating suspension, diethyl phthalate is added to the Eudragit L-30D-55 and the contents stirred until the diethyl phthalate is completely dissolved. This resulting suspension is diluted with water to obtain a suspension containing the desired proportion of solid contents. Using this enteric coating suspension, the beads are coated, for example, in a fluid bed coating system using a Wurster insert or with top spray coating, so that beads of enteric quality can be produced.

EXAMPLE 4

Tablets or capsules are prepared in which all the active agents are present in a single dosage unit formulated for immediate release. A hard gelatin capsule formulation is prepared as follows. The following ingredients are used in each capsule:

| | |
| --- | --- |
| Lovastatin | 80 mg |
| Enalapril | 40 mg |
| Aspirin | 81 mg |
| Vitamin $B_6$ | 50 mg |
| Vitamin $B_{12}$ | 1 mg |
| Folic acid | 3 mg |
| Calcium carbonate | 50 mg |
| Magnesium oxide | 50 mg |
| Magnesium carbonate | 25 mg |
| Cornstarch | 25 mg |
| Magnesium stearate | 1 mg |

The powdered ingredients are blended and sealed in a hard gelatin capsule. The quantity of the buffering agents (calcium carbonate, magnesium carbonate, magnesium oxide) can be adjusted as necessary to minimize gastrointestinal side effects and possible interactions between the active agents. It should be understood that these buffering agents can be replaced with other suitable buffering agents, if desired.

EXAMPLE 5

Tablets or capsules are prepared wherein all the active agents are separately present in protectively coated or enterically coated granules or beads. In a hard gelatin capsule dosage form, each of the active agents is granulated and coated with cellulose acetate phthalate according to well-known pharmaceutical procedures, such as those presented in Remington's, supra. The active agents are present as follows in each capsule:

| | |
|---|---|
| Pravastatin | 40 mg |
| Ramipril | 10 mg |
| Aspirin | 81 mg |
| Vitamin $B_6$ | 50 mg |
| Vitamin $B_{12}$ | 1 mg |
| Folic acid | 3 mg |

EXAMPLE 6

Each of the active agents is separately formulated into coated or uncoated compressed tablets by standard pharmaceutical techniques, and these tablets are then enclosed within a hard gelatin capsule.

EXAMPLE 7

The capsule formulation of Example 1 is used in a double-blind, placebo-controlled study of 250 subjects (N=250) who are at elevated cardiac risk. The subjects are divided into three groups: Group 1 ("Usual Care") (N=100) receives usual medical care and a daily placebo capsule; Group 2 ("Stepped-Up Risk Management") (N=100) receives usual medical care plus a daily capsule that contains 80 mg lovastatin; and Group 3 ("Aggressive Risk Management") receives usual medical care plus the tablet formulation of Example 1 for daily dosing.

Entry criteria for the study: All persons greater than 18 years old with systemic lupus erythematosus (SLE) as defined by the 1997 revised ACR criteria for SLE or who are diagnosed and followed by a member of the American College of Rheumatology will be eligible. The SLE manifestations/criteria will be recorded.

The following exclusion criteria will apply: liver disease; pregnancy, nursing, or unwillingness to use acceptable contraception; heavy alcohol consumption; concomitant cholestyramine, niacin, or erythromycin; aspirin intolerance; concomitant lithium; concomitant potassium supplement or potassium sparing diuretic; concomitant cyclosporin; history of allergy or sensitivity to ACE inhibitors; congestive heart failure; renal artery stenosis; peptic ulcer disease in last 6 months; history of intracranial bleed or brain tumor; bleeding diathesis; history of muscle disease; participation in study of another experimental agent.

The study will last five years. Approximately 10% of the subjects in each of the three groups will be given a blood pressure measuring machine and will measure and record their blood pressure once daily. Groups 2 and 3 will receive individualized patient education on reducing cardiovascular risk. Subjects in all the groups will receive the following laboratory tests:

Baseline: Blood pressure; ANA; C-reactive protein; antiphospholipid antibody; total, HDL, and LDL cholesterol; CBC; creatinine; potassium. Serum will be stored.

Three weeks: Blood pressure; SGPT; total, HDL, and LDL cholesterol; CBC; creatinine; potassium. Serum will be stored (1 red top).

Exit: Blood pressure; total, HDL, and LDL cholesterol; CBC; creatinine. Serum will be stored (1 red top).

At the completion of the study it is found that subjects in Group 2 had fewer cardiovascular events than those in Group 1, and that subjects in Group 3 had significantly fewer cardiovascular events than those in Group 2.

We claim:

1. An orally administrable pharmaceutical dosage form for treating a patient at an elevated cardiovascular risk, comprising a combination of:
    (a) a therapeutically effective daily dosage of a cholesterol-lowering agent, as a first active agent;
    (b) a therapeutically effective daily dosage of an inhibitor of the renin-angiotensin system, as a second active agent; and
    (c) a therapeutically effective daily dosage of aspirin, as a third active agent;
    wherein at least one of the active agents is present in a dosage unit that physically separates the at least one active agent from the other active agents, and
    wherein the effective daily dosage units of each of the active agents of the combination have different release profiles.

2. The dosage form of claim 1, wherein at least two of the active agents are present in dosage units that physically separate the at least two active agents from the other active agents and from each other.

3. The dosage form of claim 1, wherein the cholesterol-lowering agent is present in a first dosage unit, the inhibitor of the renin-angiotensin system is present in a second dosage unit, and the aspirin is present in a third dosage unit.

4. The dosage form of claim 3, wherein the dosage form is a capsule, and the dosage units each comprise a plurality of beads or granules contained therein.

5. The dosage form of claim 3, wherein the dosage form is a capsule, and the dosage units each comprise a tablet contained therein.

6. The dosage form of claim 3, wherein the dosage form is a compressed tablet, and the dosage units each comprise a physically isolated segment thereof.

7. The dosage form of claim 6, wherein the compressed tablet is a layered tablet, and the dosage units each comprise a layer thereof.

8. The dosage form of claim 3, wherein the dosage form is a compressed tablet, and each dosage unit comprises a plurality of beads or granules contained in an admixture therein.

9. The dosage form of claim 3, wherein the dosage form is comprised of an inner core coated with at least two concentric layers.

10. The dosage form of claim 9, containing two concentric layers.

11. The dosage form of claim 10, wherein the inner core is comprised of one of the dosage units and each concentric layer contains one of the dosage units.

12. The dosage form of claim 9, wherein the inner core is comprised of an inert material.

13. The dosage form of claim 12, containing three concentric layers.

14. The dosage form of claim 13, wherein each concentric layer contains one of the dosage units.

15. The dosage form of claim 3, wherein at least one of the dosage units is an immediate release dosage unit.

16. The dosage form of claim 15, wherein all of the dosage units are immediate release dosage units.

17. The dosage form of claim 15, wherein at least one of the dosage units is a delayed release dosage unit.

18. The dosage form of claim 15, wherein at least one of the dosage units is a sustained release dosage unit.

19. The dosage form of claim 3, wherein at least one of the dosage units is a delayed release dosage unit.

20. The dosage form of claim 19, wherein at least one of the dosage units is a sustained release dosage unit.

21. The dosage form of claim 1, further comprising at least one of vitamin $B_6$, vitamin $B_{12}$, and folic acid.

22. The dosage form of claim 1, wherein the cholesterol-lowering agent is selected from the group consisting of HMG CoA reductase inhibitors, bile acid sequestrants, probucol, fibric acid agents, and combinations thereof.

23. The dosage form of claim 1, wherein the cholesterol-lowering agent is an HMG CoA reductase inhibitor.

24. The dosage form of claim 23, wherein the HMG CoA reductase inhibitor is selected from the group consisting of atorvastatin, cerivistatin, fluindostatin, fluvastatin, lovastatin, mevastatin, pravastatin, simvastatin, and velostatin.

25. The dosage form of claim 24, wherein the HMG CoA reductase inhibitor is selected from the group consisting of lovastatin and pravastatin.

26. The dosage form of claim 25, wherein the HMG CoA reductase inhibitor is lovastatin.

27. The dosage form of claim 1, wherein the inhibitor of the renin-angiotensin system is selected from the group consisting of angiotensin converting enzyme (ACE) inhibitors and angiotensin II antagonists.

28. The dosage form of claim 27, wherein the inhibitor of the renin-angiotensin system is an ACE inhibitor.

29. The dosage form of claim 28, wherein the ACE inhibitor is selected from the group consisting of captopril, cilazapril, delapril, enalapril, fentiapril, fosinopril, indolapril, lisinopril, perindopril, pivopril, quinapril, ramipril, spirapril, trandolapril, and zofenopril.

30. The dosage form of claim 29, wherein the ACE inhibitor is selected from the group consisting of captopril, enalapril, fosinopril, lisinopril, quinapril, ramipril, and trandolapril.

31. The dosage form of claim 30, wherein the ACE inhibitor is enalapril.

32. The dosage form of claim 27, wherein the inhibitor of the renin-angiotensin system is an angiotensin II antagonist.

33. The dosage form of claim 32, wherein the angiotensin II antagonist is selected from the group consisting of losartan, irbesartan, eprosartan, candesartan, valsartan, telmisartan, zolasartin, and tasosartan.

34. The dosage form of claim 33, wherein the angiotensin II antagonist is losartan.

35. An orally administrable pharmaceutical dosage form for treating a patient at an elevated cardiovascular risk, comprising:
(a) a first dosage unit containing approximately 10 to approximately 120 mg of an HMG CoA reductase inhibitor selected from the group consisting of atorvastatin, fluvastatin, lovastatin, pravastatin, and simvastatin, as a first active agent;
(b) a second dosage unit containing approximately 1 to approximately 60 mg of an ACE inhibitor selected from the group consisting of captopril, enalapril, fosinopril, lisinopril, quinapril, ramipril, and trandolapril, as a second active agent; and
(c) a third dosage unit containing approximately 20 to approximately 600 mg aspirin, as a third active agent,
wherein each dosage unit provides physical separation between each of the active agents, thereby preventing contact therebetween, and
wherein the effective daily dosage units of each of the active agents of the combination have different release profiles.

36. The dosage form of claim 35, wherein the first and second dosage units are sustained release dosage units, and the third dosage unit is an immediate release dosage unit.

37. The dosage form of claim 35, wherein the dosage form is a capsule, and the dosage units each comprise a plurality of beads or granules contained therein.

38. The dosage form of claim 35, wherein the dosage form is a capsule, and the dosage units each comprise a tablet contained therein.

39. The dosage form of claim 35, wherein the dosage form is a compressed tablet, and the dosage units each comprise a physically isolated segment thereof.

40. The dosage form of claim 39, wherein the compressed tablet is a layered tablet, and the dosage units each comprise a layer thereof.

41. The dosage form of claim 35, wherein the dosage form is a compressed tablet, and each dosage unit comprises a plurality of beads or granules contained in an admixture therein.

42. The dosage form of claim 35, wherein the dosage form is comprised of an inner core coated with at least two concentric layers.

43. The dosage form of claim 42, containing two concentric layers.

44. The dosage form of claim 43, wherein the inner core is comprised of one of the dosage units and each concentric layer contains one of the dosage units.

45. The dosage form of claim 42, wherein the inner core is comprised of an inert material.

46. The dosage form of claim 45, containing three concentric layers.

47. The dosage form of claim 46, wherein each concentric layer contains one of the dosage units.

48. The dosage form of claim 47, wherein at least one of the dosage units is an immediate release dosage unit.

49. The dosage form of claim 48, wherein all of the dosage units are immediate release dosage units.

50. The dosage form of claim 48, wherein at least one of the dosage units is a delayed release dosage unit.

51. The dosage form of claim 48, wherein at least one of the dosage units is a sustained release dosage unit.

52. The dosage form of claim 35, wherein at least one of the dosage units is a delayed release dosage unit.

53. The dosage form of claim 50, wherein at least one of the dosage units is a sustained release dosage unit.

54. The dosage form of claim 35, further comprising at least one of vitamin $B_6$, vitamin $B_{12}$, and folic acid.

55. A packaged kit for a patient at an elevated cardiovascular risk to use in the self-administration of multiple oral dosage forms, the kit including a container housing a plurality of oral dosage forms and instructions for carrying out drug administration therewith, the improvement comprising incorporating in said oral dosage forms a combination of active agents comprised of: a therapeutically effective daily dose of a cholesterol-lowering agent, a therapeutically effective daily dose of an inhibitor of the renin-angiotensin system, a therapeutically effective daily dose of aspirin,
wherein the active agents are present in a dosage unit that physically separates at least one active agent from the other active agents, and
wherein the effective daily dose of each of the active agents of the combination have different release profiles.

56. The packaged kit of claim 55, wherein said oral dosage forms each comprise:
- (a) approximately 10 to approximately 120 mg of an MMG CoA reductase inhibitor as the cholesterol-lowering agent, wherein the HMG CoA reductase inhibitor is selected from the group consisting of atorvastatin, fluvastatin, lovastatin, pravastatin, and simvastatin;
- (b) approximately 1 to approximately 60 mg of an ACE inhibitor as the inhibitor of the renin-angiotensin system, wherein the ACE inhibitor is selected from the group consisting of captopril, enalapril, fosinopril, lisinopril, quinapril, ramipril, and trandolapril;
- (c) approximately 20 to approximately 600 mg aspirin; and
- (d) a pharmaceutically acceptable carrier.

57. The packaged kit of claim 56, wherein each of said oral dosage forms further comprises:
- (e) at least one of
  - (i) approximately 25 mg to approximately 75 mg vitamin B6,
  - (ii) approximately 0.25 to approximately 2 mg vitamin B12, and
  - (iii) approximately 1 mg to approximately 8 mg folic acid.

58. The packaged kit of claim 57, wherein the HMG CoA reductase inhibitor is lovastatin and the ACE inhibitor is enalapril.

59. The packaged kit of claim 58, wherein each of said oral dosage forms contains approximately 25 mg to approximately 75 mg vitamin B6, approximately 0.25 mg to approximately 2 mg vitamin B12, and approximately 1 mg to approximately 8 mg folic acid.

* * * * *

UNITED STATES PATENT AND TRADEMARK OFFICE
CERTIFICATE OF CORRECTION

PATENT NO.      : 6,669,955 B2
DATED           : December 30, 2003
INVENTOR(S)     : Shubha Chungi and Theodore L. Iorio It is certified that error appears in the above-identified patent and that said Letters Patent is hereby corrected as shown below:

Column 26,
Line 64, please delete "claim 15" and insert -- claim 3 --

Column 30,
Lines 3 and 13, please delete "B6" and insert -- $B_6$ --
Lines 5 and 14, please delete "B12" and insert -- $B_{12}$ --

Signed and Sealed this

Sixth Day of April, 2004

JON W. DUDAS
*Acting Director of the United States Patent and Trademark Office*

Disclaimer 6,669,955 B2—Shubha Chungi, Sharon; Theodore L. Iorio, Millis, both of MA (US). COMBINATION DOSAGE FORM CONTAINING INDIVIDUAL DOSAGE UNITS OF A CHOLESTEROL-LOWERING AGENT, AN INHIBITOR OF THE RENIN-ANGIOTENSIN SYSTEM, AND ASPIRIN. Patent Dated December 30, 2003. Disclaimer filed August 05, 2005 by Attorney of Record.

The term of this patent shall not extend beyond the expiration date of Patent No. 6,576,256.

(*Official Gazette October 3, 2006*)